United States Patent
Elistratov et al.

(10) Patent No.: US 9,974,856 B2
(45) Date of Patent: May 22, 2018

(54) METHOD OF TREATING ANDROGEN DEFICIENCY IN WOMEN

(71) Applicants: Dmitriy G. Elistratov, Penza (RU); Villory I. Strukov, Penza (RU); Vyacheslav N. Trifonov, Penza region (RU); Yuliya A. Elistratova, Penza (RU); Konstantin G. Elistratov, Penza (RU); Natalia V. Kurus', Penza (RU); Alexander V. Fyodorov, Penza region (RU); Evgeniy N. Krutyakov, Penza (RU); Elena S. Andreyeva, Penza (RU); Tatiana V. Elistratova, Penza (RU); Irina V. Khomyakova, Penza (RU); Galina A. Tolbina, Penza (RU); Galina V. Dolgushkina, Penza (RU); Alla N. Astafieva, Penza (RU); Tatiana A. Kuptsova, Penza (RU); Yuliya G. Shcherbakova, Penza (RU); Natalia M. Smirnova, Penza (RU)

(72) Inventors: Dmitriy G. Elistratov, Penza (RU); Villory I. Strukov, Penza (RU); Vyacheslav N. Trifonov, Penza region (RU); Yuliya A. Elistratova, Penza (RU); Konstantin G. Elistratov, Penza (RU); Natalia V. Kurus', Penza (RU); Alexander V. Fyodorov, Penza region (RU); Evgeniy N. Krutyakov, Penza (RU); Elena S. Andreyeva, Penza (RU); Tatiana V. Elistratova, Penza (RU); Irina V. Khomyakova, Penza (RU); Galina A. Tolbina, Penza (RU); Galina V. Dolgushkina, Penza (RU); Alla N. Astafieva, Penza (RU); Tatiana A. Kuptsova, Penza (RU); Yuliya G. Shcherbakova, Penza (RU); Natalia M. Smirnova, Penza (RU)

(73) Assignee: Parapharm Ltd., Penza (RU)

(*) Notice: Subject to any disclaimer, the term of this patent is extended or adjusted under 35 U.S.C. 154(b) by 0 days. days.

(21) Appl. No.: 15/357,151

(22) Filed: Nov. 21, 2016

(65) Prior Publication Data
US 2017/0065646 A1 Mar. 9, 2017

Related U.S. Application Data

(63) Continuation-in-part of application No. 13/512,671, filed as application No. PCT/RU2010/000613 on Oct. 21, 2010, now abandoned.

(30) Foreign Application Priority Data

Nov. 30, 2009 (RU) ............................... 2009144461

(51) Int. Cl.
*A61K 35/64* (2015.01)
*A61K 45/06* (2006.01)
*A61K 9/00* (2006.01)
*A61K 31/191* (2006.01)
*A61K 33/10* (2006.01)
*A61K 35/63* (2015.01)

(52) U.S. Cl.
CPC ............... *A61K 45/06* (2013.01); *A61K 9/00* (2013.01); *A61K 31/191* (2013.01); *A61K 33/10* (2013.01); *A61K 35/63* (2015.01); *A61K 35/64* (2013.01)

(58) Field of Classification Search
None
See application file for complete search history.

(56) References Cited

PUBLICATIONS

Strukov (Osteoporos Int (2014), vol. 25 (Suppl 2): S213-S214; p. 220).*

* cited by examiner

*Primary Examiner* — Susan Hoffman
(74) *Attorney, Agent, or Firm* — Patentagar PLLC; Alexander Rabinovich

(57) ABSTRACT

A biologically active food additive, comprising drone brood homogenate in the daily amount between 10 and 600 mg which can be combined on the weight percent basis with a calcium compound selected from calcium carbonate, calcium citrate, calcium gluconate, calcium aspartate, calcium phosphate and calcium citrate —16.67 to 93.75 wt. %; and drone brood —6.25 to 83.33 wt. %. Trials showed that administering the preparation contributes to the normalization of androgens in women resulting in the overall health improvement and disappearance or decrease of clinical signs of androgen deficiency.

3 Claims, No Drawings

METHOD OF TREATING ANDROGEN DEFICIENCY IN WOMEN

CROSS-REFERENCE TO RELATED APPLICATIONS

This application is a continuation-in-part of the pending U.S. National phase application Ser. No. 13/512,671 filed May 30, 2012, now abandoned, of the International application PCT/RU2010/000613, filed Oct. 21, 2010, claiming priority to Russian application 2009144461, filed Nov. 30, 2009, the entire contents of each of the applications being hereby incorporated into the present application by reference in full.

BACKGROUND OF THE INVENTION

1. Field of the Invention

The present invention relates to biologically active food supplements (additives) and is intended for treating androgen deficiency in women and for preventive action against the states associated with osteoporosis.

2. Description of Related Art

The problem of osteoporosis (reduction in the amount of calcium in the bone structures) is a common knowledge. In order to address this problem, calcium preparations are used based on calcium carbonate, calcium citrate, calcium gluconate, calcium aspartate, calcium ascorbate, calcium aminochelate, calcium fumarate, calcium succinate, calcium phosphate, calcium citrate and other compounds. It is known that calcium preparations are better assimilated in combination with vitamin D. Therefore, multiple drugs are known, for example, calcium gluconate tablets (registration number R No. 000140/02-2001 MZ RF), Calcium-D3 Nycomed tablets (registration number P No. 013478/01-2001), and the like.

The prior art preparations have the following drawbacks.
1) Unfortunately, all known preparations are directed only to increasing the ingress of calcium into the body rather than eliminating the reasons of the bones losing calcium.
2) When a calcium preparation is administered, calcium may enter not only the bones but also other organs and systems, in particular it may calcify concrements in the kidneys that leads to a malfunction of kidneys.

In other words, to treat osteoporosis with calcium preparations is as effective as trying to pour water into holed barrel. The ability of the body to assimilate calcium and to use the same as intended is believed to be more important than the amount of calcium entering the body.

On the other hand, it is known that an important role in preserving the density of the mineral bone stock in both young and elderly men is played by androgens, i.e. male sex hormones. A lower bone density and a higher incidence of bone fractures is observed in men suffering from hypogonadism (i.e. a reduced level of testosterone, a male sex hormone). A low testosterone level is considered one of the major causes of osteoporosis, i.e. lowered mineral bone density in men, and is hence a risk factor of fractures.

An average testosterone level in women is substantially lower than that in men so that even an insignificant decrease in the testosterone level leads to osteoporosis. This also explains why more women than men suffer from osteoporosis.

Also, testosterone is a primary androgen and as such is a precursor of estrogens. It is well known that women in the reproductive age need three sex hormones—estrogens, gestagens, and androgens. For the physiological process of aging in the postmenopausal period to run normally, two of them—estrogens and androgens are necessary. An opinion exists that disorders in the postmenopausal period are mainly caused by androgen deficiency. That the androgen receptors are present in practically all the organs and tissues of the woman's body—bone tissue, central nervous system, skin, vessels, fatty tissue, unstriated and striated muscles—argues for how badly androgens are necessary for women.

Female androgen deficiency results in the decrease of sexual drive, low mood, reduction of muscle mass, the decrease of the bone tissue density, and the decrease of the sense of well-being. A proper level of androgens may be of great importance in metabolic, psychological, and sexual functions in women. Naturally, the level of testosterone in adult male is between 300 and 1000 ng/dl, whereas in adult female it is, according to various authors, between 20-50 and 80-120 ng/dl, i.e. about one-tenth that for males. Consequently, even a moderate disorder in forming androgens and metabolism thereof may result in developing androgen-deficiency condition in females.

The main androgens in serum in females with a normal menstrual period are testosterone and dihydrotestosterone (DHT). Dehydroepiandrosterone-sulfate, dehydroepiandrosterone (DHEA) and androstenedione are considered prohormones because it is only their conversion into testosterone that shows their androgenic properties. Healthy females in their reproductive age produce 500 µg of testosterone daily (5% of its daily production in males). With age, the level of all androgens in females decreases substantially. For example, the level of total and free testosterone, androstenedione, and DHEA With regard to osteoporosis, androgens (first of all, testosterone) influence the bony tissue both directly and indirectly. The direct influence of testosterone on the bony tissue is responsible for the differences in the structure of male and female skeletons. Testosterone indirectly affects the bone formation through estrogens, female sex hormones, which are formed from androgens under the action of enzyme aromatase. Since testosterone is the primary estrogen in males, a decrease in its secretion also leads to a decrease in the bone density.

Accordingly, men with diagnosed osteoporosis are supposed to undergo hormonal examination including tests for testosterone, estradiol and sex steroid-binding globulin. In turn, all men with a low content of sex hormones need to undergo densitometry with a view to detecting osteoporosis.

Various medicaments, such as calcium preparations, vitamins D, and bisphosphonates, are used for the treatment of decreased bone density and osteoporosis. However, it has been proved that such medicaments have a minimum efficiency given that the testosterone level is still low, because the proper assimilation of medicaments directed to repairing the bone density is ensured precisely by testosterone. Therefore, the treatment of the bone density disorders has to be comprehensive, directed to both compensating for a deficit (if any) in testosterone and administering of calcium preparations.

However, when reducing this theory to practice problems have been faced with the known preparations sustaining the testosterone level in the body (for example, testosterone propionate) since they all require the most stringent health control.

The reason is that testosterone preparations are referred to doping drugs and have a lot of negative effects on the human body. When testosterone comes from the outside, the production of its own testosterone in the human body further decreases. On the other hand, as shown above, the body is in constant need for the ingress of calcium.

SUMMARY OF THE INVENTION

Therefore, it is an object of the present invention to provide a biologically active food additive for ongoing administration, which would compensate for the androgen deficiency in women.

It is also an object of the present invention to provide a biologically active food additive for ongoing administration, which would compensate for the content of calcium in the body, sustain the testosterone level and also facilitate a better assimilation of calcium and retention thereof in the body.

These objects are achieved by providing a biologically active food additive, comprising drone brood homogenate in the daily amount of between 10 and 600 mg which can be combined on the weight percent basis with a calcium compound selected from calcium carbonate, calcium citrate, calcium gluconate, calcium aspartate, calcium phosphate and calcium citrate—16.67 to 93.75 wt. %; and drone brood—6.25 to 83.33 wt. %.

The claimed biologically active food additive is available in a powdered, tablet or capsular form.

On the one hand, the technical effect of the present invention consists in providing a biologically active food additive, which sustains a normal testosterone level in the body, to ensure the efficient assimilation of calcium by the body and retention thereof in the bony tissue for a prolonged time enabling thereby the prevention of osteoporosis. On the other hand, the present invention stems from the unexpectedly uncovered fact that drone brood possesses androgenotropic properties.

DETAILED DESCRIPTION OF THE INVENTION

The use of drone brood in the present invention can be explained by the following. The drone brood is a donator of sex entomological hormones such as prolactin, estradiol, progesterone, testosterone, which stimulate the reproductive functions in men and women. Rich in hormones and vitamins not being hormone substitutes, the drone brood is effective against the hormonal background disorders, stimulates the central mechanisms for regulating the rate of androgen formation and excludes possible replacement therapy. The studies conducted in the Apiculture Scientific-Research Institute (Rybnoye, Ryazan region, Russia) demonstrated the safe use of the drone brood and also proved the gonadotropic effect of the drone brood on the stimulation of central links controlling the testosterone synthesis. (Krivtsov N. I. et al., Theory and Methods of Apitherapy, Moscow, 2007). Therefore, the testosterone level in the body may be sustained using the drone brood.

The impact of drone brood upon the male body has been studied substantially well. It is the stimulation of the function of the testicles to produce testosterone that explained that impact. With that in view, the use of drone brood to stimulate producing testosterone in women, especially in postmenopausal age, was not believed to be obvious considering that it was not clear which body organ should be stimulated to produce testosterone in women. It has been known that androgens are produced in women either by suprarenal cortex or by ovaries. But with regard to women in the postmenopausal age, the latter way of the synthesis of testosterone falls down because of the general decline of the functions of this organ. As to the former way of synthesizing androgens, the adrenal glands synthesize androstenedione, dehydroepiandrosterone and 11-β-hydroxyandrostenedione. These hormones are known to be precursors of testosterone. The authors of the present invention have put forward an assumption that it is the liver that promotes producing testosterone in women breaking the entomological testosterone down to human testosterone (Phylippovich Yu. B., Physiological fundamentals of human vital activities. Moscow, Vlados, 2005, p. 336). But no matter what the way of synthesizing testosterone in women is, it does not seem possible to be drawing parallels with the ways of synthesizing this hormone in men.

It has been known, for example, that all steroids are compounds of a lipid nature. They are poorly soluble in water, and in blood for that reason they are in relation with blood plasma proteins, with only insignificant portion thereof being free. It is just the free steroids that are highly active biologically: they cross membranes of target cells. Cholesterol is a precursor of steroids, and it turns into progesterone in suprarenal cortex cells. Progesterone in turn can evolve into corticosteroids, androgens and estrogens (Lyubimova Z. V., Age specific physiology, part 1, Moscow, Vlados, 2004, p. 105).

One of dietary advices to raise the level of testosterone in men is to increase the amount of the cholesterol consumed. For women, however, this recommendation cannot take place because it can entail an increase of estrogens or corticosteroids. It has been also known that endocrine glands in men and women, when identically stimulated, behave differently in synthesizing hormones. For example, releasing follitropin by hypophysis results in producing estrogens in women and testosterone in men (Hurovetz G. V., Age specific anatomy and physiology, Moscow, Vlados, 2013, p. 215). Thus, despite the fact that drone brood has been known to act in men as an activator of producing their own testosterone, it was not to be expected, with differences in functioning of the endocrine systems in men and women in view, that the matters influencing the central components responsible for synthesizing testosterone in men will behave similarly in women. Even more so, it is not to be expected that the matters regulating production of testosterone in testicles will influence the testosterone production in women.

The present invention is based on an unexpected discovery of the fact that drone brood shows androgenotropic effect in women. The technical result of the invention is the increasing in blood in women of the level of their own androgens, particularly testosterone.

Previously, it was uncovered that drone brood was a donator of various sex hormones (estradiol, progesterone, testosterone) in men and women (RU2498811, Nov. 20, 2013; RU2412616, Feb. 27, 2011; RU2497533, Nov. 10, 2013). At that time, however, it was not known yet which of those hormones are donated by drone brood in women. Not disclosed in those publications is the information that administering drone brood to women will result in raising the level of testosterone in their blood. From what was known, it was logical to deduct that it will be the level of estradiol or progesterone that will raise in women. Various sources inform about a pronounced gonadotropic action of drone brood, which stimulates the activity of the sex glands. It has been known that the drone brood homogenate appears as a stimulator of the central mechanisms regulating the production of the male sex hormones (androgens), restores biochemical characteristics of male gonads (the concentration of testosterone in blood and of fructose in the spermatocyst liquid), prostate, as well as sperm production. In men, the use of drone brood is effective in sex dysfunction and infertility and enhances libido. In women, taking drone brood homogenate stimulates the function of ovaries and enables restoring the endocrine profile and reproductive performance. In other words, it has been known from a number of publications that the drone brood homogenate stimulates production of androgens in men and of estrogens in women. Those publications relate to treating osteoporosis. It has been known that osteoporosis in women can have estradiol-related nature. Summing up the above, the inventors believe that prior art discloses no solution that results in achieving the above-stated technical result—the increasing in blood in women of the level of their own androgens, particularly testosterone—upon using biologically active supplements, in particular drone brood. With that, it was found that the operation of entomological testosterone differs substantially from that of exogenous testosterone, such as testosterone propionate, which when used becomes very hurtful to the woman's health resulting in masculinization, acne, voice coarseness, hypertrichosis, baldness, clitoromegaly, thrombophilia. Taking into account that the liver breaks testosterone propionate down to estrogens, it would be illogical to expect that entomological testosterone of drone brood will be broken down in the liver to human testosterone.

The authors of the present invention developed a preparation based on drone brood homogenate to be made in a tablet, capsule or powder form. The homogenate can be combined with a calcium compound including a pharmacologically active calcium compound chosen from a series comprising calcium carbonate, calcium citrate, calcium gluconate, calcium aspartate, calcium amino acid chelate, calcium fumarate, calcium succinate, calcium ascorbate, calcium phosphate, or any combination thereof. In this preparation, the calcium compound is in the amount of 16.67-93.75 weight % and the drone brood is in the amount of 6.25-83.33 weight %.

Also, a trial was performed to explore how this preparation act upon hormonal state of women having androgen deficiency. Since 2009 to March of 2013, 72 women in the age range of 49-85 were examined. Only women with androgen deficiency confirmed hormonally and clinically were included in the trial. The trial included a physical examination, a general laboratory examination, as well as a hormonal examination—estimation of testosterone and sex hormone-binding globulin (SHBG). The IMMULITE 2000 Immunoassay System was employed for the hormonal examination with the use of immunochemiluminometric assay. All the women were divided into two groups comparable in terms of age and severity of the disease. The first group, 38 women, had been taking the claimed preparation orally, one tablet (100 mg of drone brood in a tablet) in the morning and for the night, for three months, thrice a year. The second, control group (34 women) had been taking placebo under the same regimen.

A statistical review of the data obtained was undertaken using the StatSoft, Windows XP software package. Quantitative characters were described by mean and mean root square deviations. The results were presented in the M±m format, where M is an arithmetic average and m—an error in mean. Differences were considered statistical ones where significance value p<0.05. Noted after the termination of the course of treatment were mood improvement, increment in activity, increase of muscle power, decrease of dysuric symptoms, decrease of osteoporosis activity. None of that was noted in the women of the second group. The hormonal examination showed that before the treatment the total testosterone concentration in women was 1.1±0.4 nmole/l for the first group and 1.2±0.5 nmole/l for the second group (p>0.05), the reference concentration for this method being 1.7-3.4 nmole/l. The SHBG concentration in the first and second groups before the treatment were 64.3±2.6 nmole/l and 62.8±2.9 nmole/l (p>0.05), respectively.

29 out of 37 patients noted amelioration of signs after 9 months of the treatment with the claimed preparation. When assessed, the lab values showed the increasing of total testosterone concentration in blood plasm from 1.1±0.4 nmole/l to 2.5±0.6 nmole/l (p<0.05), the SHBG concentration from 64.3±2.6 nmole/l to 115.0±5.9 nmole/l (p<0.05). In the second group taking placebo, no patient showed any positive shift in testosterone content and HSBG increase.

The results of the conducted trial make it clear that administering the claimed preparation contributes to the normalization of androgens in women resulting in the overall health improvement and disappearance or decrease of clinical signs of androgen deficiency. The effect can be reached at when the daily dosage of the preparation is between 10 and 600 mg. The obtained data demonstrate that aging comes with the decrease of the hormonal androgen status that brings about androgen deficiency symptoms onset.

Although the components forming part of the inventive biologically active food additive are known in the folk or traditional medicine, their combination in one product to treat osteoporosis is not disclosed in the prior art.

The combined use of the mentioned components enables a more efficient assimilation of calcium by the body since calcium not only enters the body but is also retained in the bony tissue thanks to the drone brood. It has been found that the drone brood is able to improve the assimilability of calcium by the body and to retain the same in the bony tissue for a long time, i.e. to ensure a prolonged effect of the bony tissue calcium intake. In addition, the administration of calcium together with the drone brood makes it possible to lower the dosage of the calcium compounds, to thus prevent lithogenesis in the kidneys as well as other negative effects of taking the calcium preparations (for example, gastroenteric upsets) from occurring.

The ratio of the calcium compound and the drone brood varies within a wide range. The range width is determined by the individual parameters: age, gender, state of health and other factors.

It is known that the upper acceptance limit for the administration of calcium is 1000-1500 mg per day. Due to the combined administration of the drone brood and the calcium compound, the daily dosage of calcium may be lowered since the bioavailability (assimilability) of calcium is improved and bone resorption (calcium depletion) is prevented.

Based on the foregoing, the maximum consumption of calcium is suggested to be 600 mg.

The minimum consumption of calcium is determined by the minimum body need for ionized calcium, that being of 200 mg.

The maximum consumption of the drone brood to prevent osteoporosis is determined by the expediency of use and is 1000 mg.

The minimum consumption of the drone brood to prevent osteoporosis is 40 mg (see RU2233666 C1, Oct. 8, 2004) and is determined by the pharmacological activity.

Therefore, the administration range of the components forming the biologically active food additive according to the present invention is as follows: drone brood: 40 to 1000 mg or 6.25% to 83.33%; calcium: 200 to 600 mg or 16.67% to 93.75%.

Therefore, the combined use of the drone brood and calcium compound in the additive makes it possible to reduce significantly the maximum (upper) daily consumption of calcium from 1500 mg to 600 mg thereby reducing the negative side effects of calcium on the human body and widening the group of persons able to use calcium preparations. The reduction in the maximum daily consumption of calcium is necessary because an opposite disease, hypercalcemia, quiet often occurs in cases where calcium preparations are administered in the doses of 1000 to 1500 mg. For example, of the 1000 patients continuously receiving preparations against osteoporosis, 86 had hypermineralization of the 1 to 3 degree (Strukov V. I., Actual Problems of Osteoporosis, Penza, 2009, Rostra Publishers).

The above-identified quantitative ratio makes it possible to ensure an optimum ingress of calcium for each individual and its most complete assimilation thanks to the claimed amount of the drone brood, which ensures a certain content of sulfhydryl enzyme groups in the additive, as well as testosterone, progesterone, prolactin and estradiol. The drone brood is rich in amino acids. The amino acids in turn act as transporters of calcium to the cell (Strukov V. I., Ibid.). In order for calcium to be assimilated, vitamins A, C, E, D and micronutrient elements, such as magnesium, copper, zinc, phosphorus are also required. All of them are present in the drone brood.

As a result, all calcium being administered is completely assimilated by the bony tissue. Surprisingly, it has been found that the retention of calcium in the bony tissue for a prolonged time is provided by a certain amount of sulfhydryl enzyme groups in the drone brood, vitamins D and E so that the process of its depletion slows down. Besides, a long period of the normal bony tissue density is accounted for by a sufficiently high content of phosphorus in the drone brood which enters the body in the amount specified above, thereby facilitating the assimilation of calcium.

Therefore, the problem of not only saturating the bony tissue with calcium but also of retaining the same for a long time therein has been solved for the first time by means of the combined use of the calcium preparations and the drone brood in the claimed ratio. The risk of fractures has been considerably lessened as compared to the prior art preparations since a 5% increase in the mineral bone density leads to a 35% reduction in the risk of fracture, and the additional antiresorptive feature of the claimed preparation reduces the risk of fracture by another 20%.

In order to prepare the biologically active food additive in accordance with the present invention, there is provided a powdered calcium compound selected from calcium carbonate, calcium citrate, calcium gluconate, calcium aspartate, calcium phosphate, calcium citrate at a concentration of 16.67 wt. % to 93.75 wt. % and is mixed with a drone brood at a concentration of 6.25 wt. % to 83.33 wt. % until a homogeneous mixture is formed. The resulting mixture is then tableted or capsulated. The biologically active food additive presents a homogeneous light beige powder with a humidity of 1 to 3.5%, which is further subjected to tableting or capsulation. A tablet or a capsule contains 1 g of the mixture.

When preparing the biologically active food additive, the drone brood is used in the form of a lyophilizate. In order to obtain a lyophilizate, the larval drone brood is homogenized using a mixer. The homogenate comprises a thick yellow creamy liquid with a characteristic odor. The content of dry matter in the homogenate does not exceed 22.5%. The lyophilizate is obtained by freezing the homogenate for 2-3 hours at a temperature of minus 35-40° C. followed by vacuum sublimation at a residual pressure of 0.1-0.6 mm hg for 40-48 hours and bringing the temperature to 25-30° C. by the end of lyophilization. The lyophilizate includes a powder whose color varies from beige to yellow, with a high hygroscopicity and residual moisture content of 1-3.5%. In other words, the preparation conditions of lyophilizate are such that the solid matter composition of the drone brood homogenate may be preserved without changes except for the moisture content.

Provided below are the examples of preparing the biologically active food additive.

EXAMPLE 1

17 kg of powdered calcium gluconate was provided and mixed with 83 kg of the drone brood lyophilizate. The mixture was then stirred to homogeneity and the resulting product was capsulated.

EXAMPLE 2

90 kg of powdered calcium carbonate was provided and mixed with 10 kg of the drone brood lyophilizate. The mixture was stirred to homogeneity and then tableted.

For prevention of osteoporosis, one capsule of the biologically active food additive is administered 3 times a day for one month separately from meals. A one-month break in the administration should be provided. The serum calcium value does not reduce during this period. In other words, the calcium content is sustained at a normal level.

The above technical effect is demonstrated by way of the following examples.

EXAMPLE 1

A human subject, female, born in 1959. The mineral bone density of T–1.4 was measured in the distal antibrachium by means of the forearm scanner DXT-200 available from Osteometer MediTech, Inc. Osteopenia was diagnosed and 1 g of calcium gluconate was administered 3 times a day. A six-month course of preventive medication was conducted. A re-evaluation six months later showed a reduced bone density down to T–1.6. That is, the mineral bone density (MBD) became less. After a one-month break in the administration, the serum calcium value was below the normal value.

For reference: MBD normal value—the values of T criterion with a standard deviation of +1 to –1 from the peak bone mass;

$1^{st}$ degree osteopenia—MBD of –1 to –1.5;
$2^{nd}$ degree osteopenia—MBD of –1.5 to –2;
$3^{rd}$ degree osteopenia—MBD of –2 to –2.5;
$1^{st}$ degree osteoporosis—MBD of –2.5 and less without fractures;
$2^{nd}$ degree osteoporosis—MBD of –2.5 and less with osteoporotic bone fractures.

The densitometric T scale presents the number of standard deviations up and down an average bone mass value. The T criterion decreases in parallel with a gradual reduction in the bone mass with age and is used to evaluate the MBD in adults.

EXAMPLE 2

The same female human subject with diagnosed osteopenia and the mineral bone density of T –1.6 was administered one capsule of the claimed biologically active food additive 3 times a day A six-month preventive medication course was conducted following the pattern of one-month administration/one-month break. The mineral bone density increased to T −1.2. The serum calcium value normalized. No reduction in the serum calcium value was observed during the re-examination performed three months later.

Therefore, apart from sustaining the normal testosterone level and compensating for the deficit of calcium in the body, the inventive biologically active food additive according to the present invention also facilitates a more efficient assimilation of calcium and retention thereof in the bony tissue for a long time (i.e. has a prolonged activity) and thus is believed to be an excellent preparation for the prevention of osteoporosis.

The invention claimed is:

1. A method of treating androgen deficiency in women comprising the steps of providing a drone brood homogenate and administering the drone brood homogenate in the amount between 10 and 600 mg daily.

2. The method as claimed in claim 1, wherein the drone brood is combined with a pharmacologically active calcium compound and wherein the calcium compound is in the amount of 16.67-93.75 weight % and the drone brood is in the amount of 6.25-83.33 weight %.

3. The method as claimed in claim 2, wherein the pharmacologically active calcium compound is chosen from a series consisting of calcium carbonate, calcium citrate, calcium gluconate, calcium aspartate, calcium amino acid chelate, calcium fumarate, calcium succinate, calcium ascorbate, calcium phosphate, or any combination thereof.

* * * * *

UNITED STATES PATENT AND TRADEMARK OFFICE
CERTIFICATE OF CORRECTION

PATENT NO. : 9,974,856 B2
APPLICATION NO. : 15/357151
DATED : May 22, 2018
INVENTOR(S) : Elistratov et al.

It is certified that error appears in the above-identified patent and that said Letters Patent is hereby corrected as shown below:

Column 2 Lines 30-32 delete "For example, the level of total and free testosterone, androstenedione, and DHEA"

Signed and Sealed this
Twelfth Day of June, 2018

Andrei Iancu
*Director of the United States Patent and Trademark Office*